(12) United States Patent
Shimmel et al.

(10) Patent No.: US 6,811,556 B2
(45) Date of Patent: *Nov. 2, 2004

(54) MICROKERATOME BLADE

(75) Inventors: Jeffrey T. Shimmel, Deltona, FL (US); George A. Kocar, Orlando, FL (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/235,328

(22) Filed: Sep. 5, 2002

(65) Prior Publication Data

US 2003/0191485 A1 Oct. 9, 2003

Related U.S. Application Data

(63) Continuation-in-part of application No. 10/114,808, filed on Apr. 3, 2002.

(51) Int. Cl.[7] .................................................. A61F 9/00
(52) U.S. Cl. ....................................... 606/166; 604/170
(58) Field of Search ................................ 606/166, 167, 606/161, 171, 172, 4, 5, 6; 604/22, 170

(56) References Cited

U.S. PATENT DOCUMENTS

| | | | |
|---|---|---|---|
| 4,662,370 A | 5/1987 | Hoffmann et al. | |
| 4,784,135 A | 11/1988 | Blum et al. | |
| 4,903,695 A | 2/1990 | Warner | |
| 5,133,726 A | 7/1992 | Ruiz et al. | |
| 5,258,002 A | * 11/1993 | Jeffers et al. | 606/167 |
| 5,288,292 A | 2/1994 | Giraud et al. | |
| 5,342,378 A | 8/1994 | Giraud et al. | |
| 5,376,099 A | 12/1994 | Ellis et al. | |
| 5,496,339 A | 3/1996 | Koepnick | |
| 5,586,980 A | 12/1996 | Kremer | |
| 5,591,174 A | 1/1997 | Clark et al. | |
| 5,595,570 A | 1/1997 | Smith | |
| 5,624,456 A | 4/1997 | Hellenkamp | |
| 5,817,115 A | 10/1998 | Nigam | |
| 5,980,543 A | 11/1999 | Carriazo et al. | |
| 6,051,009 A | 4/2000 | Hellenkamp et al. | |
| 6,071,293 A | 6/2000 | Krumeich | |
| 6,254,619 B1 | * 7/2001 | Garabet et al. | 606/166 |
| 6,345,622 B1 | * 2/2002 | Chandler et al. | 128/849 |
| 2003/0018347 A1 | 1/2003 | Pallikaris et al. | |
| 2003/0018348 A1 | 1/2003 | Pallikaris et al. | |

FOREIGN PATENT DOCUMENTS

EP   1 181 913 A2   2/2002

\* cited by examiner

*Primary Examiner*—David O. Reip
*Assistant Examiner*—Victor Nguyen
(74) *Attorney, Agent, or Firm*—Jeffrey S. Schira

(57) ABSTRACT

A microkeratome blade for use for the removal of the epithelial layer and underlying Basement Membrane while leaving a smooth and undisturbed Bowman's Membrane in preparation for a laser refractive surgical procedure. The blade is capable of cutting through the epithelial layer and Basement Membrane, but not capable of cutting through Bowman's Membrane.

6 Claims, 3 Drawing Sheets

MICROKERATOME BLADE

This application is a continuation-in-part of U.S. patent application Ser. No. 10/114,808, filed Apr. 3, 2002, currently co-pending.

BACKGROUND OF THE INVENTION

This invention relates generally to the field of refractive surgery and, more particularly, to microkeratomes used for performing laser refractive surgery.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea also may be asymmetric or toric, resulting in an uncompensated cylindrical refractive error referred to as corneal astigmatism. In addition, due to age-related reduction in lens accommodation, the eye may become presbyopic resulting in the need for a bifocal or multifocal correction device.

In the past, axial myopia, axial hyperopia and corneal astigmatism generally have been corrected by spectacles or contact lenses, but there are several refractive surgical procedures that have been investigated and used since 1949. Jose Barraquer, M.D. investigated a procedure called keratomileusis that reshaped the cornea using a microkeratome and a cryolathe. This procedure was never widely accepted by surgeons. Another procedure that has gained widespread acceptance is radial and/or transverse incisional keratotomy (RK or AK, respectively). In the 1990s, the use of photoablative lasers to reshape the surface of the cornea (photorefractive keratectomy or PRK) or for mid-stromal photoablation (Laser-Assisted In Situ Keratomileusis or LASIK) have been approved by regulatory authorities in the U.S. and other countries. Recently, a new version of PRK called Laser Epithelial Keratomileusis (LASEK) has been developed wherein the epithelial layer is soaked in alcohol so as to release it from Bowman's Membrane and the epithelial layer is non-destructively rolled aside and the underlying stromal tissue is ablated in a manner similar to PRK. This procedure does not always allow for the smooth removal of the epithelial layer in a single sheet. In addition, alcohol is toxic to corneal tissue.

Accordingly, a need continues to exist for a device and method for the safe, consistent removal of the epithelial layer and Basement Membrane during a laser refractive surgical procedure.

BRIEF SUMMARY OF THE INVENTION

The present invention improves upon the prior art by providing a microkeratome blade for use for the removal of the epithelial layer and underlying Basement Membrane while leaving a smooth and undisturbed Bowman's Membrane in preparation for a laser refractive surgical procedure. The blade is capable of cutting through the epithelial layer and Basement Membrane, but not capable of cutting through Bowman's Membrane.

Accordingly, one objective of the present invention is to provide a safe and non-toxic method for the removal of the epithelial layer and underlying Basement Membrane in preparation for a laser refractive surgical procedure.

Another objective of the present invention is to provide a method for the removal of the epithelial layer in preparation for a laser refractive surgical procedure without the use of toxic chemicals.

Another objective of the present invention is to provide a device that provides the safe and non-toxic method for the removal of the epithelial layer and underlying Basement Membrane in preparation for a laser refractive surgical procedure.

Another objective of the present invention is to provide a microkeratome blade that provides the safe and non-toxic method for the removal of the epithelial layer and underlying Basement Membrane in preparation for a laser refractive surgical procedure.

These and other advantages and objectives of the present invention will become apparent from the detailed description and claims that follow.

DETAILED DESCRIPTION OF THE INVENTION

Figure 1:
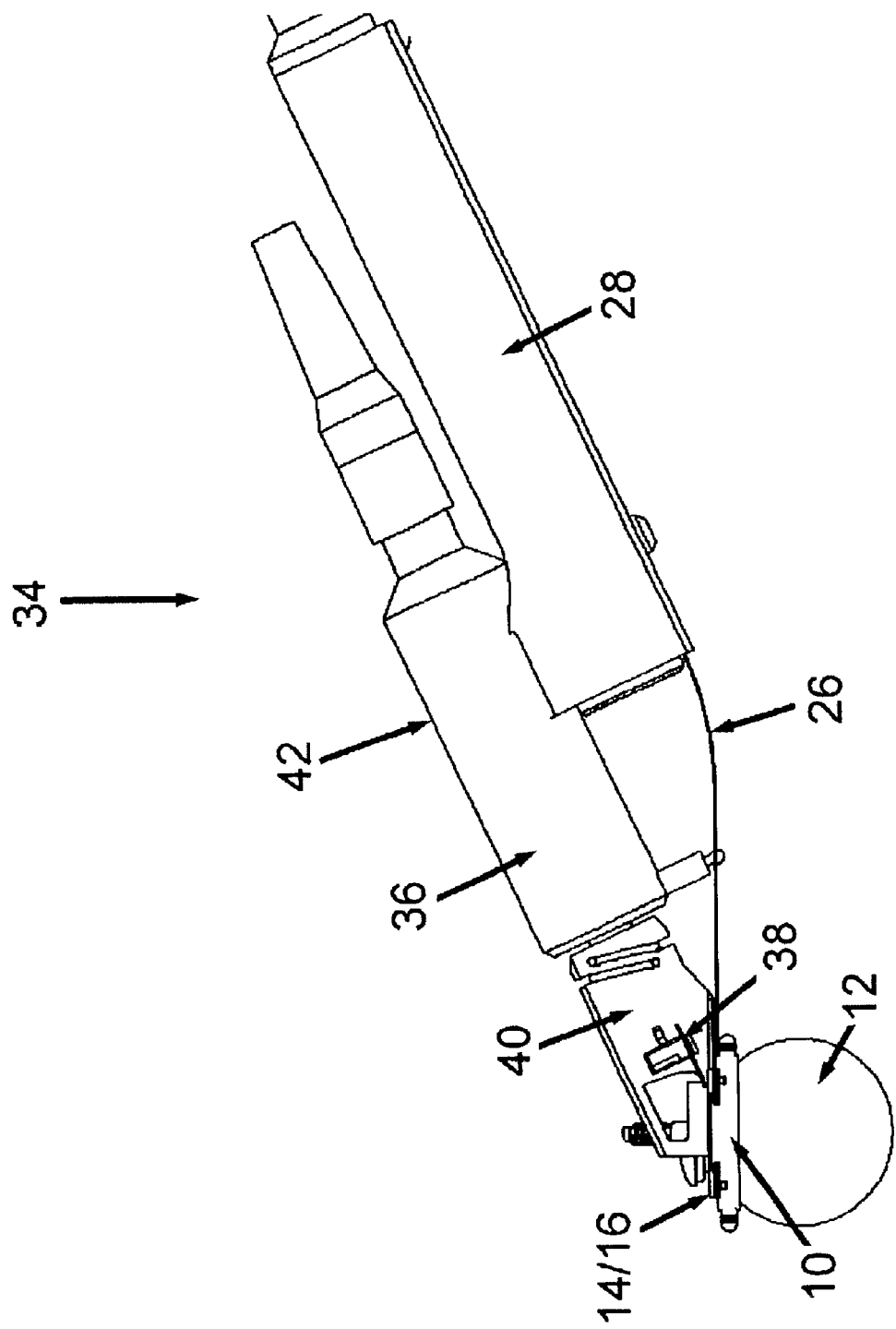
FIG. 1 is a schematic representation of a microkeratome that may be used with the invention of the present method.

As best seen in FIG. 1, one microkeratome 34 that may be used with the method of the present invention generally includes suction ring 10 sized and shaped so as to affix to eye 12. Ring 10 includes guides 14/16 opposite eye 12 that guide cutting head 40 across ring 10. Ring 10 is connected through translation member 26 to stepper motor 28 for providing linear movement of cutting head 40 across ring 10. Cutting head 40 contains blade 38 that is eccentrically connected to motor 36 contained within housing 42 of microkeratome 34. Microkeratome 34 is well known in the art (see for example U.S. Pat. No. 6,071,293 (Krumeich), the entire contents of which being incorporated herein by reference), and commercially available from sources such as Alcon Laboratories, Inc., Fort Worth, Tex.

Figure 2:
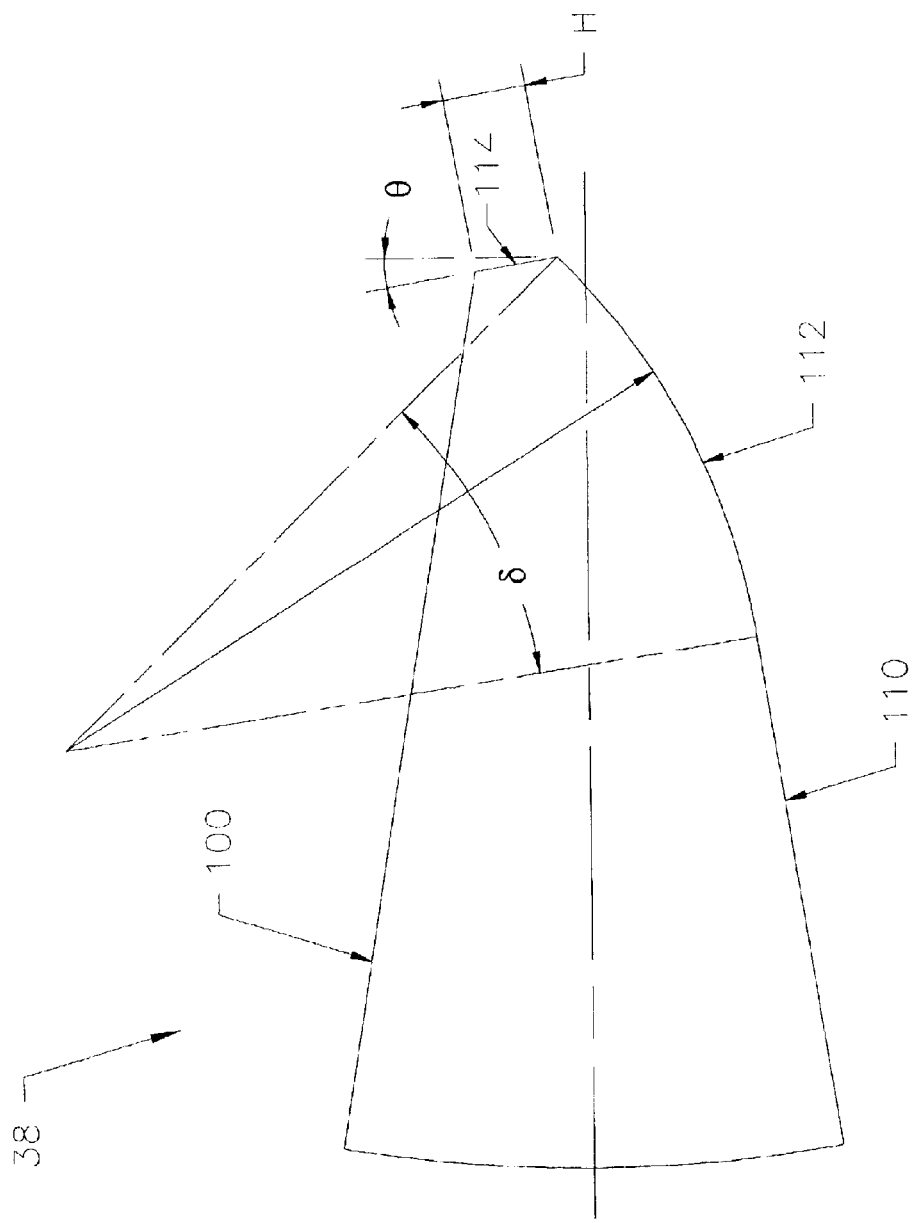
FIG. 2 is an enlarged partial side view of the microkeratome blade of the present invention.

As best seen in FIG. 2, blade 38 generally includes relatively flat side 100, tapered side 110 containing rounded section 112 and blunt cutting edge 114 connecting flat side 100 and rounded section 112. Rounded section 112 generally has a radius of between about 0.025 millimeters and 0.200 millimeters and is rounded through of angle δ of between approximately 5 degrees and 60 degrees. Blunt cutting edge 114 generally has a height H of between approximately 0.001 millimeters and 0.050 millimeters, with between about 0.005 millimeters and 0.025 millimeters being preferred, and is ground at an offset angle Θ relative to rounded portion 112 at between approximately between 0 degrees and 60 degrees, with between approximately between 0 degrees and 20 degrees being preferred. Preferably, rounded section 112 and blunt tip 114 have a textured surface finish. Blade 38 may be made of any suitable material, such as 400 Series stainless steel and may be made using conventional surgical blade manufacturing techniques well known in the art.

Figure 3:
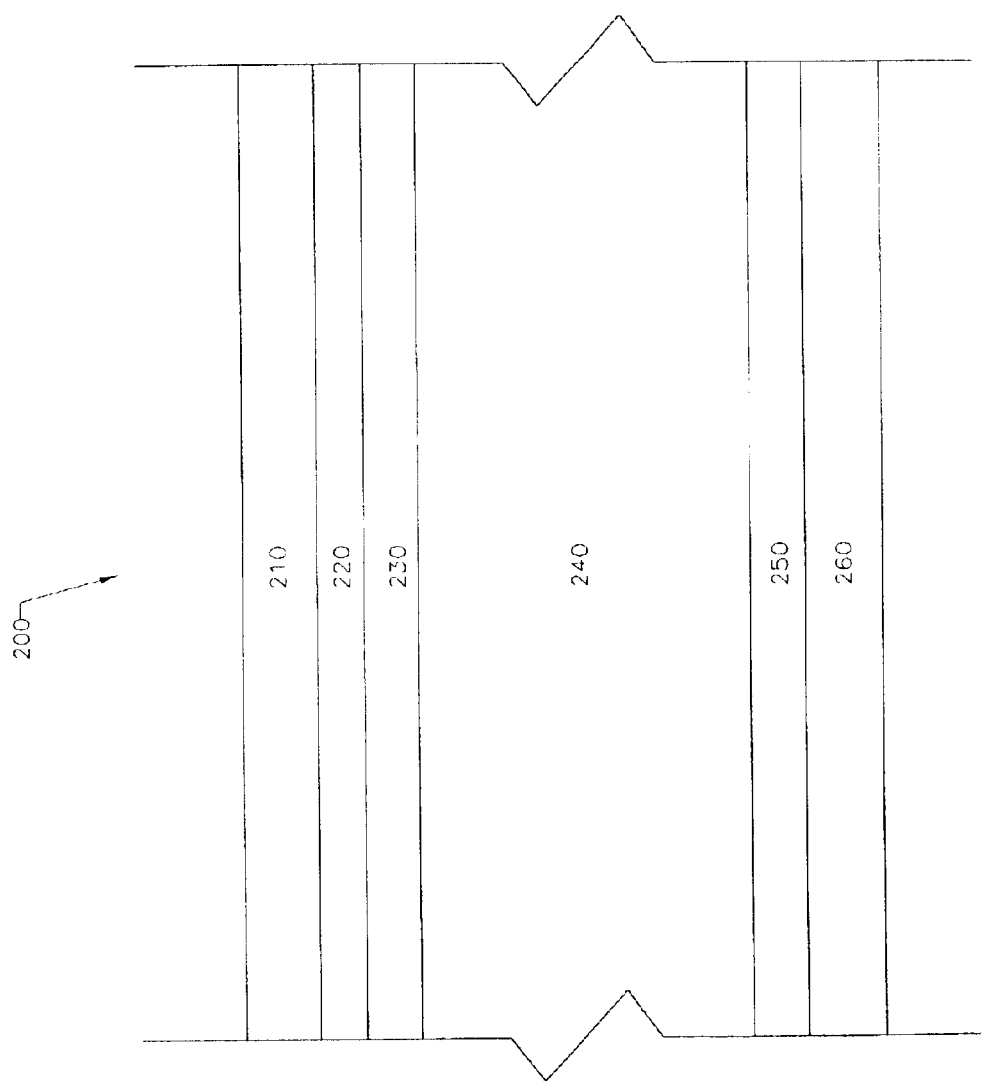
FIG. 3 is a partial cross-sectional view of a human cornea.

As best seen in FIG. 3, human cornea 200 has several layers. The outermost layer is epithelium 210, followed by Basement Membrane 220, Bowman's Membrane 230, substantia propria or stroma 240, Descemet's Membrane 250 and endothelium 260. The method of the present invention involves the use of microkeratome 34 having blade 38 to remove epithelium 210 and Basement Membrane 220 while leaving Bowman's Membrane 230 relatively intact. The method of the present invention uses microkeratome 34 in a conventional manner well known to those skilled in the art. Preferably, the intraocular pressure of the eye undergoing the surgical procedure is briefly raised to around 80 mm Hg or greater. The oscillation frequency of blade 38 preferably is approximately between 5,000 revolutions/minute and 20,000 revolutions/minute, with approximately between 8,000 revolutions/minute and 14,000 revolutions/minute being most preferred. The speed of blade 38 as it traverses cornea 200 preferably is approximately between 1.0 millimeter/second and 2.0 millimeters/second, with approximately 1.5 millimeters/second being most preferred. As blade 38 approaches cornea 200, blunt cutting edge 114 penetrates epithelium 210 and Basement Membrane 220, but is insufficiently sharp to penetrate Bowman's Membrane 230. As a result, blunt cutting edge 114 and rounded portion 112 scrape along the surface of Bowman's Membrane 230, separating epithelium 210 and Basement Membrane 220 from Bowman's Membrane 230 without damaging Bowman's Membrane 230. Following such separation, Bowman's Membrane 230 and stroma 240 are irradiated as in a conventional laser refractive surgical procedure, see for example, U.S. Pat. No. 4,784,135 (Blum, et al.) and U.S. Pat. No. 4,903,695 C1 (Warner, et al.), the entire contents of which being incorporated herein by reference.

This description is given for purposes of illustration and explanation. It will be apparent to those skilled in the relevant art that changes and modifications may be made to the invention described above without departing from its scope or spirit.

We claim:

1. A microkeratome blade, comprising:
   a flat lower surface;
   an upper surface that tapers toward the lower surface, the upper surface having a rounded portion; the rounded portion having a textured surface finish; and a blunt cutting edge comprising a substantially flat surface, wherein the blunt cutting edge is disposed between the lower surface and the rounded portion of the upper surface, the blunt cutting edge having a textured surface finish.

2. The microkeratome blade of claim 1 wherein the rounded portion has a radius of between about 0.025 millimeters and 0.200 millimeters.

3. The microkeratome blade of claim 1 wherein the blunt cutting edge has a height of between approximately 0.001 millimeters and 0.050 millimeters.

4. The microkeratome blade of claim 3 wherein the blunt cutting edge has a height of between approximately 0.005 millimeters and 0.025 millimeters.

5. The microkeratome blade of claim 1 wherein the blunt cutting edge is ground at an offset angle relative to the rounded portion at between approximately between 0 degrees and 60.

6. The microkeratome blade of claim 5 wherein the blunt cutting edge is ground at an offset angle relative to rounded portion of approximately between 0 degrees and 20 degrees.

* * * * *

UNITED STATES PATENT AND TRADEMARK OFFICE
CERTIFICATE OF CORRECTION

PATENT NO. : 6,811,556 B2
DATED : November 2, 2004
INVENTOR(S) : Shimmel et al.

It is certified that error appears in the above-identified patent and that said Letters Patent is hereby corrected as shown below:

Column 2,
Line 51, "is rounded through of angle" should read -- is rounded through an angle --

Signed and Sealed this

First Day of February, 2005

JON W. DUDAS
*Director of the United States Patent and Trademark Office*